US011547466B2

(12) United States Patent
Sharma et al.

(10) Patent No.: US 11,547,466 B2
(45) Date of Patent: Jan. 10, 2023

(54) VISUALIZATION DEVICES AND METHODS FOR USE IN SURGICAL PROCEDURES

(71) Applicant: COVIDIEN LP, Mansfield, MA (US)

(72) Inventors: Ashish Sharma, Denver, CO (US); Claire E. Benjamin, Boulder, CO (US); Chip G. W. Bollendonk, Littleton, CO (US); John A. Hammerland, III, Arvada, CO (US); Eric R. Larson, Boulder, CO (US); William H. Nau, Jr., Longmont, CO (US); Anthony B. Ross, Boulder, CO (US); Kathryn G. Thompson, Broomfield, CO (US); Nick C. Ortiz, Boulder, CO (US); Scott C. Oubre, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 709 days.

(21) Appl. No.: 16/420,520

(22) Filed: May 23, 2019

(65) Prior Publication Data

US 2019/0388141 A1  Dec. 26, 2019

Related U.S. Application Data

(60) Provisional application No. 62/687,356, filed on Jun. 20, 2018.

(51) Int. Cl.
*A61B 18/14* (2006.01)
*A61B 18/08* (2006.01)
(Continued)

(52) U.S. Cl.
CPC ........ *A61B 18/1442* (2013.01); *A61B 18/085* (2013.01); *A61B 17/320016* (2013.01);
(Continued)

(58) Field of Classification Search
CPC .............. A61B 18/1442; A61B 18/085; A61B 2018/00601; A61B 1/05; A61B 1/00066;
(Continued)

(56) References Cited

U.S. PATENT DOCUMENTS 2,011,169 A   8/1935   Wappler
2,028,635 A   1/1936   Wappler
(Continued)

FOREIGN PATENT DOCUMENTS

DE   19906260 A1   9/1999
EP   0565822 A2   10/1993
(Continued)

OTHER PUBLICATIONS

EP Office Action for EP 02744699 dated Apr. 6, 2009.
(Continued)

*Primary Examiner* — Joseph A Stoklosa
*Assistant Examiner* — Marina Delaney Templeton
(74) *Attorney, Agent, or Firm* — Carter, DeLuca & Farrell LLP

(57) ABSTRACT

A surgical device includes a handle assembly, an elongated portion, an end effector, a visualization device, and a constant horizon mechanism. The elongated portion extends distally from the handle assembly and defines a longitudinal axis. The end effector is rotatable about the longitudinal axis relative to the handle assembly. The visualization device defines a visualization axis. A first portion of the visualization device extends through the elongated portion, and a second portion of the visualization device is disposed at least partially within the handle assembly. The visualization device is rotatable about the longitudinal axis relative to the handle assembly. The constant horizon mechanism is disposed in operative engagement with the visualization device and is configured to prevent the visualization device from (Continued)

rotating about the visualization axis when the visualization device rotates about the longitudinal axis.

12 Claims, 7 Drawing Sheets

(51) Int. Cl.
    *A61B 90/00*          (2016.01)
    *A61B 17/32*          (2006.01)
    *A61B 18/00*          (2006.01)

(52) U.S. Cl.
    CPC .............. *A61B 2018/0063* (2013.01); *A61B 2018/00345* (2013.01); *A61B 2018/00601* (2013.01); *A61B 2090/0811* (2016.02)

(58) Field of Classification Search
    CPC ..... A61B 1/0052; A61B 1/0014; A61B 1/018; A61B 1/00121; A61B 1/00128; A61B 1/00052; A61B 1/00174; A61B 1/0669; A61B 1/00181; A61B 1/00101; A61B 1/0008; A61B 2090/0811; A61B 2090/306; A61B 90/30; G02B 23/2461; G02B 23/2484
    USPC ......................................................... 600/137
    See application file for complete search history.

(56) References Cited

U.S. PATENT DOCUMENTS

| | | |
|---|---|---|
| 3,659,606 A | 5/1972 | Reimels |
| 3,764,427 A | 10/1973 | Reimels |
| 3,788,325 A | 1/1974 | Jacobsen |
| 4,052,980 A | 10/1977 | Grams et al. |
| 4,528,982 A | 7/1985 | Wellenstam |
| 4,655,217 A | 4/1987 | Reed |
| 5,011,489 A | 4/1991 | Salem |
| 5,013,312 A | 5/1991 | Parins et al. |
| 5,373,840 A | 12/1994 | Knighton |
| 5,395,384 A | 3/1995 | Duthoit et al. |
| 5,522,827 A | 6/1996 | Combs et al. |
| 5,571,172 A | 11/1996 | Chin |
| 5,591,183 A | 1/1997 | Chin |
| 5,593,418 A | 1/1997 | Mollenauer |
| 5,601,581 A | 2/1997 | Fogarty et al. |
| 5,601,589 A | 2/1997 | Fogarty et al. |
| 5,607,441 A | 3/1997 | Sierocuk et al. |
| 5,653,722 A | 8/1997 | Kieturakis |
| 5,658,282 A | 8/1997 | Daw et al. |
| 5,667,480 A | 9/1997 | Knight et al. |
| 5,676,636 A | 10/1997 | Chin |
| 5,690,668 A | 11/1997 | Fogarty et al. |
| 5,695,514 A | 12/1997 | Chin |
| 5,702,417 A | 12/1997 | Hermann |
| 5,707,382 A | 1/1998 | Sierocuk et al. |
| 5,716,325 A | 2/1998 | Bonutti |
| 5,722,934 A | 3/1998 | Knight et al. |
| 5,725,479 A | 3/1998 | Knight et al. |
| 5,730,748 A | 3/1998 | Fogarty et al. |
| 5,738,628 A | 4/1998 | Sierocuk et al. |
| 5,759,150 A | 6/1998 | Konou et al. |
| 5,762,604 A | 6/1998 | Kieturakis |
| 5,772,576 A | 6/1998 | Knighton et al. |
| 5,782,753 A | 7/1998 | DeFonzo et al. |
| 5,782,854 A | 7/1998 | Hermann |
| 5,797,946 A | 8/1998 | Chin |
| 5,797,947 A | 8/1998 | Mollenauer |
| 5,800,540 A | 9/1998 | Chin |
| 5,803,903 A | 9/1998 | Athas et al. |
| 5,814,059 A | 9/1998 | Hart et al. |
| 5,814,060 A | 9/1998 | Fogarty et al. |
| 5,817,013 A | 10/1998 | Ginn et al. |
| 5,823,946 A | 10/1998 | Chin |
| 5,827,318 A | 10/1998 | Bonutti |
| 5,836,945 A | 11/1998 | Perkins |
| D403,066 S | 12/1998 | DeFonzo |
| 5,843,104 A | 12/1998 | Samuels |
| 5,853,417 A | 12/1998 | Fogarty et al. |
| RE36,043 E | 1/1999 | Knighton |
| 5,871,496 A | 2/1999 | Ginn et al. |
| 5,873,889 A | 2/1999 | Chin |
| 5,876,413 A | 3/1999 | Fogarty et al. |
| 5,891,140 A | 4/1999 | Ginn et al. |
| 5,893,858 A | 4/1999 | Spitz |
| 5,893,866 A | 4/1999 | Hermann et al. |
| 5,895,353 A | 4/1999 | Lunsford et al. |
| 5,899,912 A | 5/1999 | Eaves, III |
| 5,899,913 A | 5/1999 | Fogarty et al. |
| 5,902,315 A | 5/1999 | DuBois |
| 5,902,316 A | 5/1999 | Mollenauer |
| 5,913,818 A | 6/1999 | Co et al. |
| 5,913,866 A | 6/1999 | Ginn et al. |
| 5,913,870 A | 6/1999 | DeFonzo et al. |
| 5,916,233 A | 6/1999 | Chin |
| 5,922,004 A | 7/1999 | DuBois |
| 5,928,135 A | 7/1999 | Knight et al. |
| 5,928,137 A * | 7/1999 | Green ................. A61B 1/3132 600/160 |
| 5,928,138 A | 7/1999 | Knight et al. |
| 5,938,680 A * | 8/1999 | Ginn ................ A61B 17/00008 606/190 |
| 5,944,734 A | 8/1999 | Hermann et al. |
| 5,951,584 A | 9/1999 | Hermann |
| 5,954,731 A * | 9/1999 | Yoon .................... A61B 17/062 606/144 |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,979,452 A | 11/1999 | Fogarty et al. |
| 5,980,549 A | 11/1999 | Chin |
| 5,984,937 A | 11/1999 | Morse et al. |
| 5,993,384 A | 11/1999 | Lunsford et al. |
| 5,993,466 A * | 11/1999 | Yoon .................... A61B 17/062 606/144 |
| 5,993,472 A | 11/1999 | Hermann et al. |
| 6,004,340 A | 12/1999 | Hermann et al. |
| 6,013,090 A | 1/2000 | Fogarty et al. |
| 6,019,771 A | 2/2000 | Bennett et al. |
| 6,022,313 A | 2/2000 | Ginn et al. |
| 6,030,396 A | 2/2000 | Samuels |
| 6,030,406 A | 2/2000 | Davis et al. |
| 6,036,713 A | 3/2000 | Kieturakis |
| 6,036,714 A | 3/2000 | Chin |
| 6,042,538 A | 3/2000 | Puskas |
| 6,051,013 A | 4/2000 | Mollenauer |
| 6,059,802 A | 5/2000 | Ginn |
| 6,068,639 A | 5/2000 | Fogarty et al. |
| 6,071,232 A | 6/2000 | Knighton et al. |
| 6,077,289 A | 6/2000 | Mollenauer |
| 6,080,102 A | 6/2000 | Konou et al. |
| 6,110,170 A | 8/2000 | Taylor et al. |
| 6,129,661 A | 10/2000 | Iafrati et al. |
| 6,139,489 A | 10/2000 | Wampler et al. |
| 6,143,008 A | 11/2000 | Eaves, III |
| 6,162,173 A | 12/2000 | Chin et al. |
| 6,174,313 B1 | 1/2001 | Bonutti |
| 6,193,651 B1 | 2/2001 | DeFonzo |
| 6,193,653 B1 | 2/2001 | Evans et al. |
| 6,196,968 B1 | 3/2001 | Rydin et al. |
| 6,203,557 B1 | 3/2001 | Chin |
| 6,203,559 B1 | 3/2001 | Davis et al. |
| 6,206,823 B1 | 3/2001 | Kolata et al. |
| 6,206,899 B1 | 3/2001 | Ginn |
| 6,221,007 B1 | 4/2001 | Green |
| 6,228,024 B1 | 5/2001 | Co et al. |
| 6,240,924 B1 | 6/2001 | Fogarty et al. |
| 6,264,670 B1 | 7/2001 | Chin |
| 6,277,064 B1 * | 8/2001 | Yoon .................... A61B 1/00177 600/104 |
| 6,277,137 B1 | 8/2001 | Chin |

(56) References Cited

U.S. PATENT DOCUMENTS

| | | |
|---|---|---|
| 6,283,963 B1 | 9/2001 | Regula |
| 6,319,265 B1 | 11/2001 | Ginn |
| 6,322,499 B1 | 11/2001 | Evans et al. |
| 6,348,037 B1 | 2/2002 | Chin et al. |
| 6,350,236 B1 | 2/2002 | Hipps et al. |
| 6,375,665 B1 | 4/2002 | Nash et al. |
| 6,413,208 B1 | 7/2002 | Schollhorn et al. |
| 6,428,468 B1 | 8/2002 | Knighton et al. |
| 6,428,556 B1 | 8/2002 | Chin |
| 6,432,044 B1 | 8/2002 | Lunsford et al. |
| 6,436,116 B1 | 8/2002 | Spitz et al. |
| 6,436,118 B1 | 8/2002 | Kayan |
| 6,443,159 B1 | 9/2002 | Fogarty et al. |
| 6,443,970 B1 | 9/2002 | Schulze et al. |
| 6,447,529 B2 | 9/2002 | Fogarty et al. |
| 6,451,035 B1 | 9/2002 | Fogarty et al. |
| 6,453,906 B1 | 9/2002 | Taylor et al. |
| 6,454,784 B1 | 9/2002 | Mollenauer |
| 6,468,206 B1 | 10/2002 | Hipps et al. |
| 6,482,153 B1 | 11/2002 | Hipps et al. |
| 6,506,200 B1 | 1/2003 | Chin |
| 6,511,494 B1 | 1/2003 | Knighton et al. |
| 6,527,771 B1 | 3/2003 | Weadock et al. |
| 6,527,787 B1 | 3/2003 | Fogarty et al. |
| 6,551,335 B1 | 4/2003 | Bardeau et al. |
| 6,572,615 B2 | 6/2003 | Schulze et al. |
| 6,592,582 B2 | 7/2003 | Hess et al. |
| 6,592,604 B2 | 7/2003 | Hess et al. |
| 6,596,010 B1 | 7/2003 | Hermann et al. |
| 6,607,547 B1 | 8/2003 | Chin |
| 6,616,661 B2 | 9/2003 | Wellman et al. |
| 6,623,482 B2 | 9/2003 | Pendekanti et al. |
| 6,648,815 B2 | 11/2003 | Schoellhorn et al. |
| 6,652,521 B2 | 11/2003 | Schulze |
| 6,656,176 B2 | 12/2003 | Hess et al. |
| 6,660,016 B2 | 12/2003 | Lindsay |
| 7,083,618 B2 | 8/2006 | Couture et al. |
| 7,101,371 B2 | 9/2006 | Dycus et al. |
| 7,645,289 B2 | 1/2010 | Bayer |
| 2003/0195544 A1 | 10/2003 | Hess et al. |
| 2003/0212420 A1 | 11/2003 | Gruhl et al. |
| 2004/0133228 A1* | 7/2004 | Bayer ................ A61B 18/1445 606/190 |
| 2005/0096670 A1 | 5/2005 | Wellman et al. |
| 2008/0154091 A1* | 6/2008 | Dejima ................ A61B 1/018 600/104 |
| 2008/0255589 A1 | 10/2008 | Blakeney et al. |
| 2014/0357952 A1 | 12/2014 | Krohn et al. |

FOREIGN PATENT DOCUMENTS

| | | |
|---|---|---|
| EP | 1399071 B1 | 3/2004 |
| WO | 9939632 A1 | 8/1999 |
| WO | 03000139 A1 | 1/2003 |
| WO | 03013365 A1 | 2/2003 |
| WO | 03013367 A2 | 2/2003 |
| WO | 2018170904 A1 | 9/2018 |

OTHER PUBLICATIONS

Extended European Search Report for U.S. Appl. No. 15/189,623 dated Mar. 17, 2016.

Extended European Search Report for application No. 16180494.3 dated Dec. 23, 2016.

European Examination Report for application No. 15 189 623.0 dated Jun. 7, 2018 (5 pages).

Extended European Search Report for Application No. 19 18 1208 dated Nov. 25, 2019.

* cited by examiner

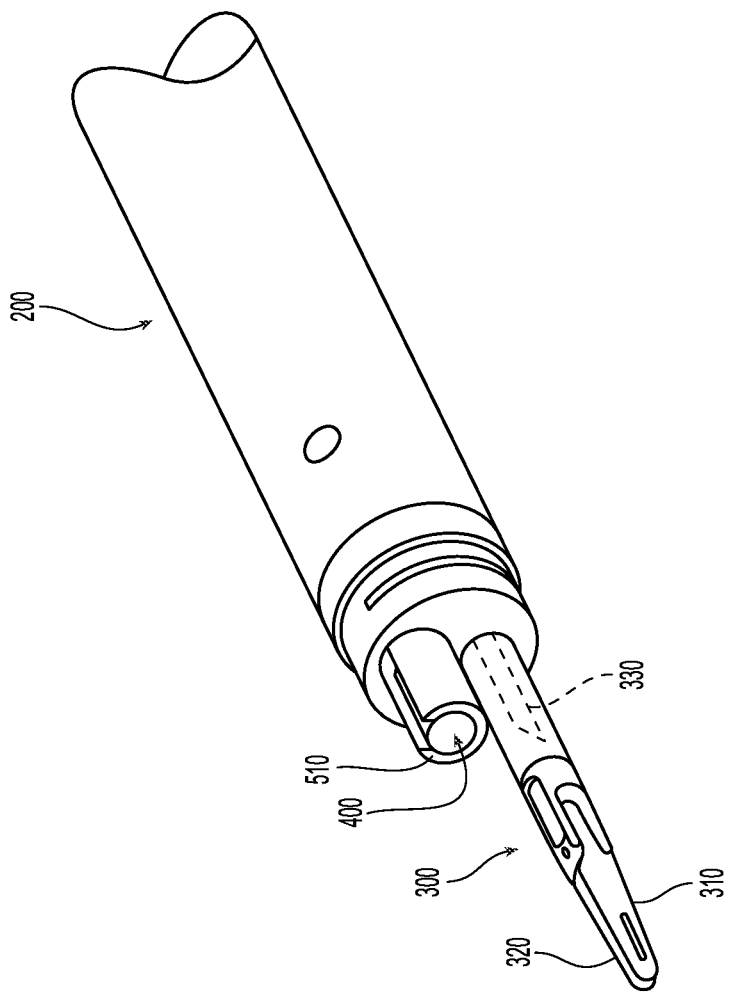
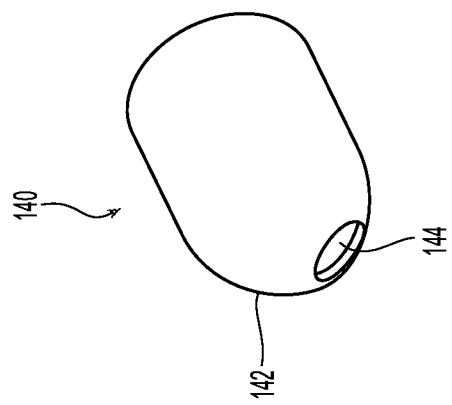
*Fig. 2*

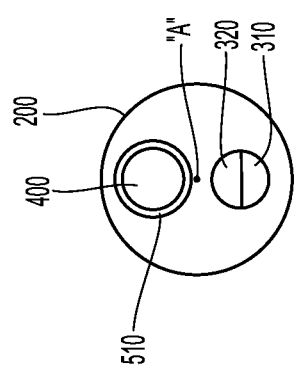
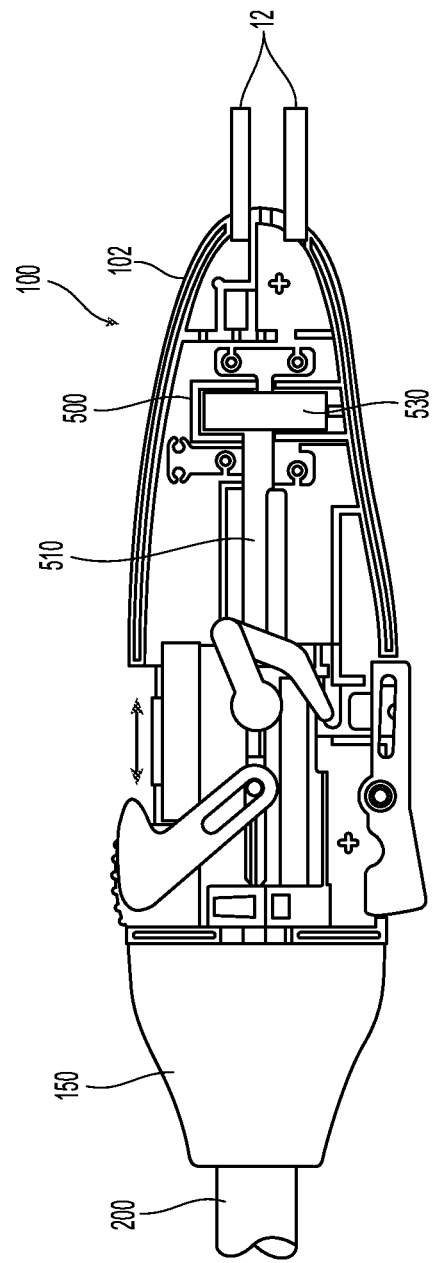

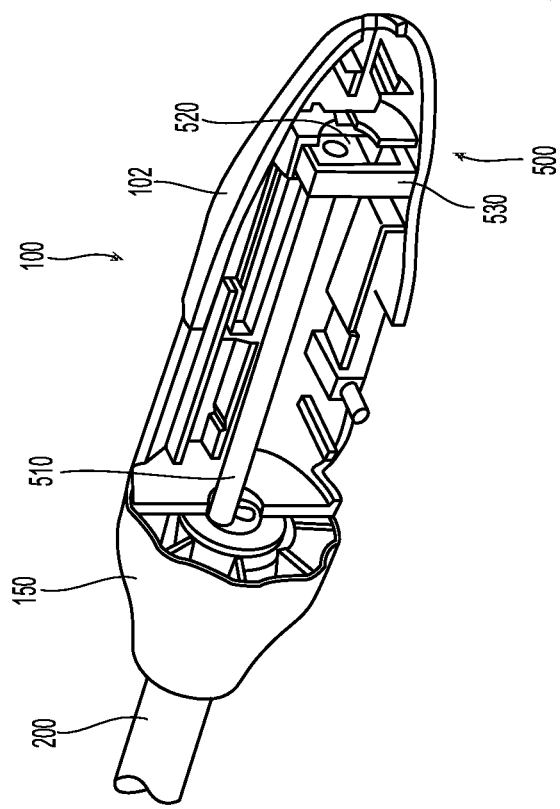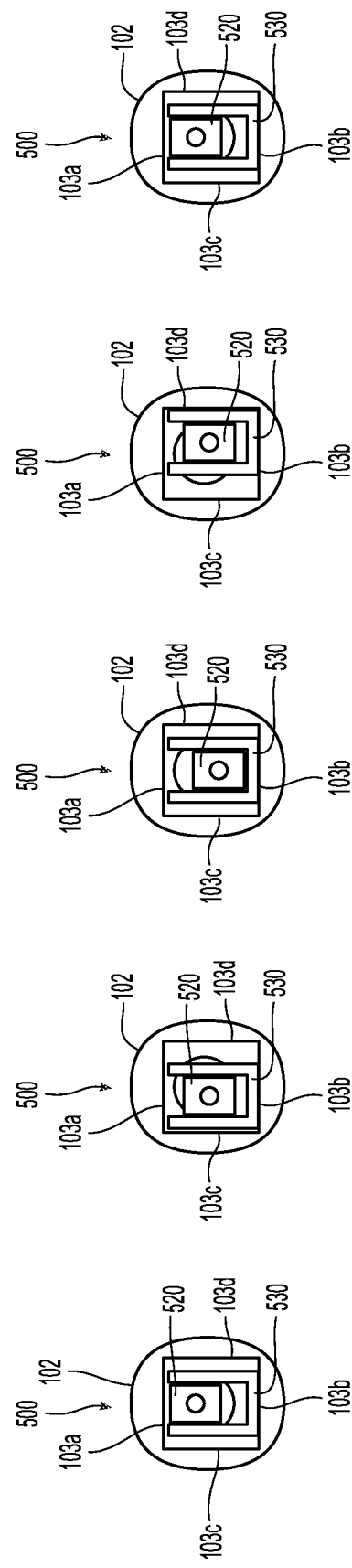

VISUALIZATION DEVICES AND METHODS FOR USE IN SURGICAL PROCEDURES

CROSS REFERENCE TO RELATED APPLICATION

The present application claims the benefit of and priority to U.S. Provisional Application Ser. No. 62/687,356, filed on Jun. 20, 2018 the entire contents of which are incorporated herein by reference.

BACKGROUND

The present disclosure relates to devices and methods for use during surgical procedures, in particular, to devices and methods to enhance visualization during surgical procedures.

TECHNICAL FIELD

Many surgical procedures benefit from the use of a visualization device during the surgical procedure. Such visualization devices help provide the surgeon with a view of the target tissue during manipulation of the distal end of the surgical instrument, for instance. Further, to minimize the number of incisions in the patient, and to reduce the number of instruments that are necessary to be within the patient during a surgical procedure, surgical instruments including a visualization device have been developed. Utilizing a surgical instrument including a visualization device typically negates the need for a separate visualization device to be inserted into a patient.

Also, the end effectors or distal ends of some surgical instruments have the ability to rotate about an axis defined by an elongated portion of the surgical instrument. When such a rotatable surgical instrument includes a visualization device on or within its distal end, the corresponding rotation of the visualization device may impede the surgeon's ability to effectively visualize the surgical site. Accordingly, it may be useful to provide a surgical instrument including a rotatable distal end, a visualization device on or within the distal end, but where at least a portion of the visualization device does not rotate upon rotation of the distal end and/or where a horizon as viewed from the visualization device remains constant upon rotation of the distal end of the surgical instrument. Such a visualization device may be referred to as a "constant horizon" device. Moreover, it may be particularly useful to provide a vein harvesting device including a "constant horizon" visualization device since vein harvesting procedures often require prodding and rotation of a distal end of the surgical device during the surgical procedure.

SUMMARY

The present disclosure relates to a surgical device including a handle assembly, an elongated portion, an end effector, a visualization device, and a constant horizon mechanism. The elongated portion extends distally from the handle assembly and defines a longitudinal axis. The end effector is disposed adjacent a distal end of the elongated portion and is configured to treat tissue. The end effector is rotatable about the longitudinal axis relative to the handle assembly. The visualization device defines a visualization axis. A first portion of the visualization device extends through the elongated portion, and a second portion of the visualization device is disposed at least partially within the handle assembly. The visualization device is rotatable about the longitudinal axis relative to the handle assembly. The constant horizon mechanism is disposed in operative engagement with the visualization device and is configured to prevent the visualization device from rotating about the visualization axis when the visualization device rotates about the longitudinal axis.

In aspects according to the present disclosure, the constant horizon mechanism includes an elongated tube, a first bushing and a second bushing. In aspects, the elongated tube extends through the elongated portion and is disposed about the visualization device. In further aspects, the elongated tube is fixed from rotation about the longitudinal axis relative to the visualization device.

In yet other aspects, the first bushing and the second bushing are disposed within the handle assembly, and the proximal portion of the elongated tube is operatively connected to the first bushing. In yet additional aspects, the elongated tube is fixed from rotation about the longitudinal axis relative to the first bushing.

In still other aspects, the first bushing is disposed at least partially within the second bushing, and the first bushing is fixed from lateral movement relative to the second bushing. In aspects, the second bushing is fixed from vertical movement relative to the handle assembly. The proximal portion of the elongated tube may be operatively connected to the first bushing, and the elongated tube may be fixed from rotation about the longitudinal axis relative to the first bushing.

In other aspects, the first bushing may be a rectangular prism and the second bushing may be generally U-shaped having three linear sides.

In yet other aspects, the visualization axis is offset from the longitudinal axis, and the visualization axis is parallel to the longitudinal axis.

Aspects of the present disclosure also relates to a method of performing a surgical procedure. The method includes positioning an end effector of a surgical device adjacent tissue and rotating the end effector about a longitudinal axis and relative to a handle assembly of the surgical device, where the longitudinal axis is defined by an elongated portion of the surgical device. The method further includes rotating a visualization device of the surgical device about the longitudinal axis with respect to the handle assembly and maintaining a rotational position of the visualization device relative to a visualization axis extending through the visualization device.

In aspects the method includes rotating the visualization device includes moving a first bushing of a constant horizon mechanism in a first direction relative to the handle assembly, and moving a second bushing of the constant horizon mechanism in a second direction relative to the handle assembly. In aspects, the first direction is perpendicular to the second direction. In yet other aspects, the first bushing is prevented by the second bushing from moving in the second direction relative to the second bushing and the second bushing may be prevented from moving in the first direction relative to the handle assembly.

In still other aspects, the visualization axis is offset from and parallel to the longitudinal axis.

BRIEF DESCRIPTION OF THE DRAWINGS

Various embodiments of the surgical devices are described herein with reference to the drawings wherein:

FIG. 2 is an enlarged perspective view of a distal portion of the vessel harvesting device of FIG. 1A, or, alternatively, FIG. 1B;

FIG. 5 is an enlarged cross-sectional view of the distal portion of the vessel harvesting device of FIG. 1A, or, alternatively, FIG. 1B;

FIG. 6 is a cut-away view of a handle assembly of the vessel harvesting device of FIG. 1B;

FIG. 7 is a perspective view of the handle assembly of the vessel harvesting device of FIG. 1A;

FIGS. 8A-8E are enlarged cross-sectional views of a constant horizon mechanism of the vessel harvesting devices of FIGS. 1A and 1B shown during different stages of operation.

DETAILED DESCRIPTION

Figure 1A:
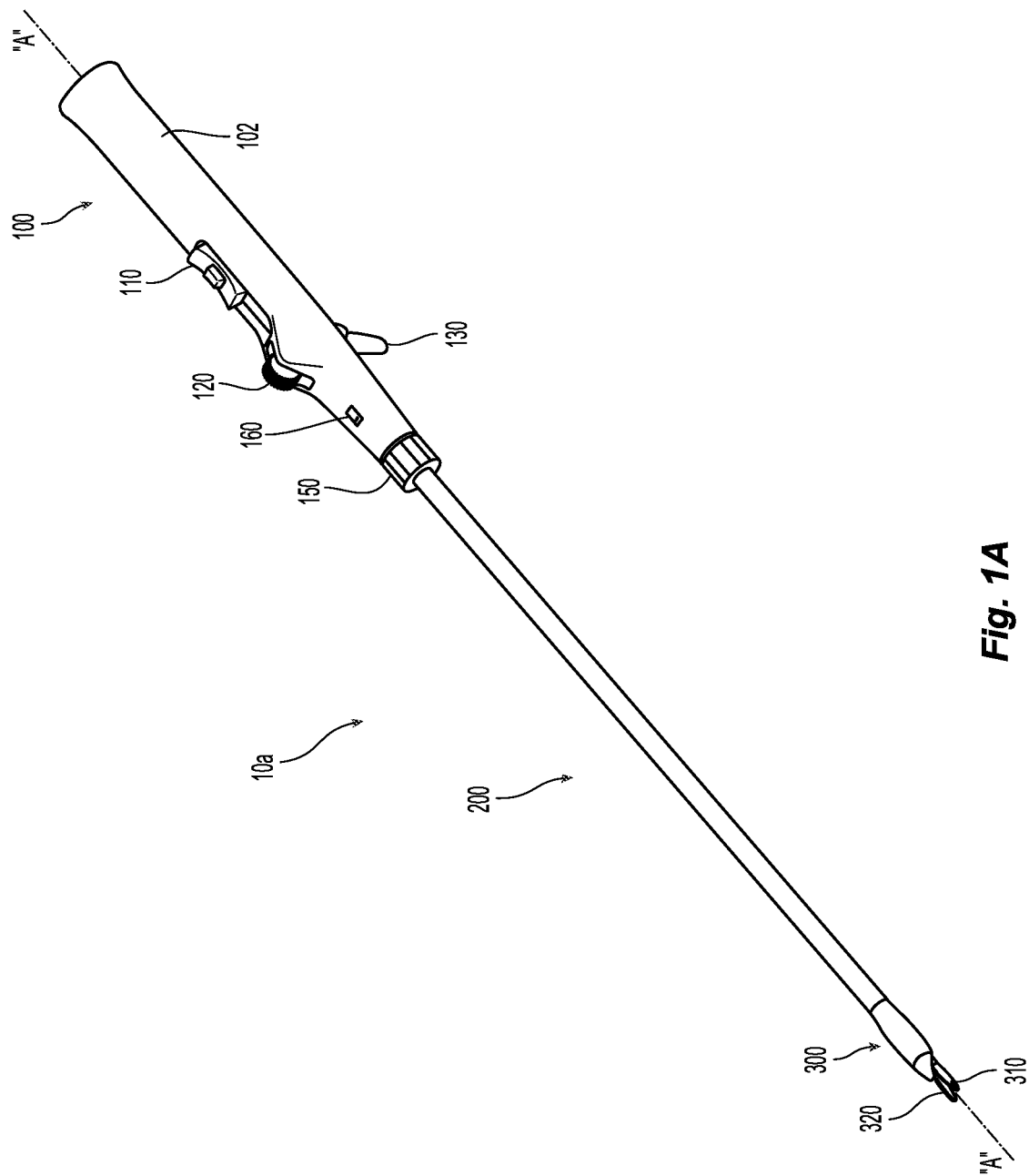
FIG. 1A is a perspective view of a vessel harvesting device in accordance with embodiments of the present disclosure.

Embodiments of the presently disclosed visualization devices for use with various surgical devices, e.g., vessel harvesting devices, are described in detail with reference to the drawings, in which like reference numerals designate identical or corresponding elements in each of the several views. As used herein the term "distal" refers to that portion of the device is farther from the user, while the term "proximal" refers to that portion of the device that is closer to the user.

While a vein harvesting device is described herein as an example of a surgical device, other types of surgical devices are usable with the visualization devices and other various features disclosed herein and are therefore included in the present disclosure.

The saphenous vein has a number of tributary veins that carry venous blood into the vein. These tributaries are typically tied off and/or cut off of the saphenous vein before the saphenous vein can be removed. In medical terms, these tributaries must be ligated and divided. When a tributary or side branch is encountered, the surgeon can use endoscopic and laparoscopic tools to close the tributaries and cut them from the saphenous vein. The tributaries can then be separated from the vein after the entire vein is stripped, or the surgeon may choose to separate the tributaries as they are encountered.

Figure 1B:
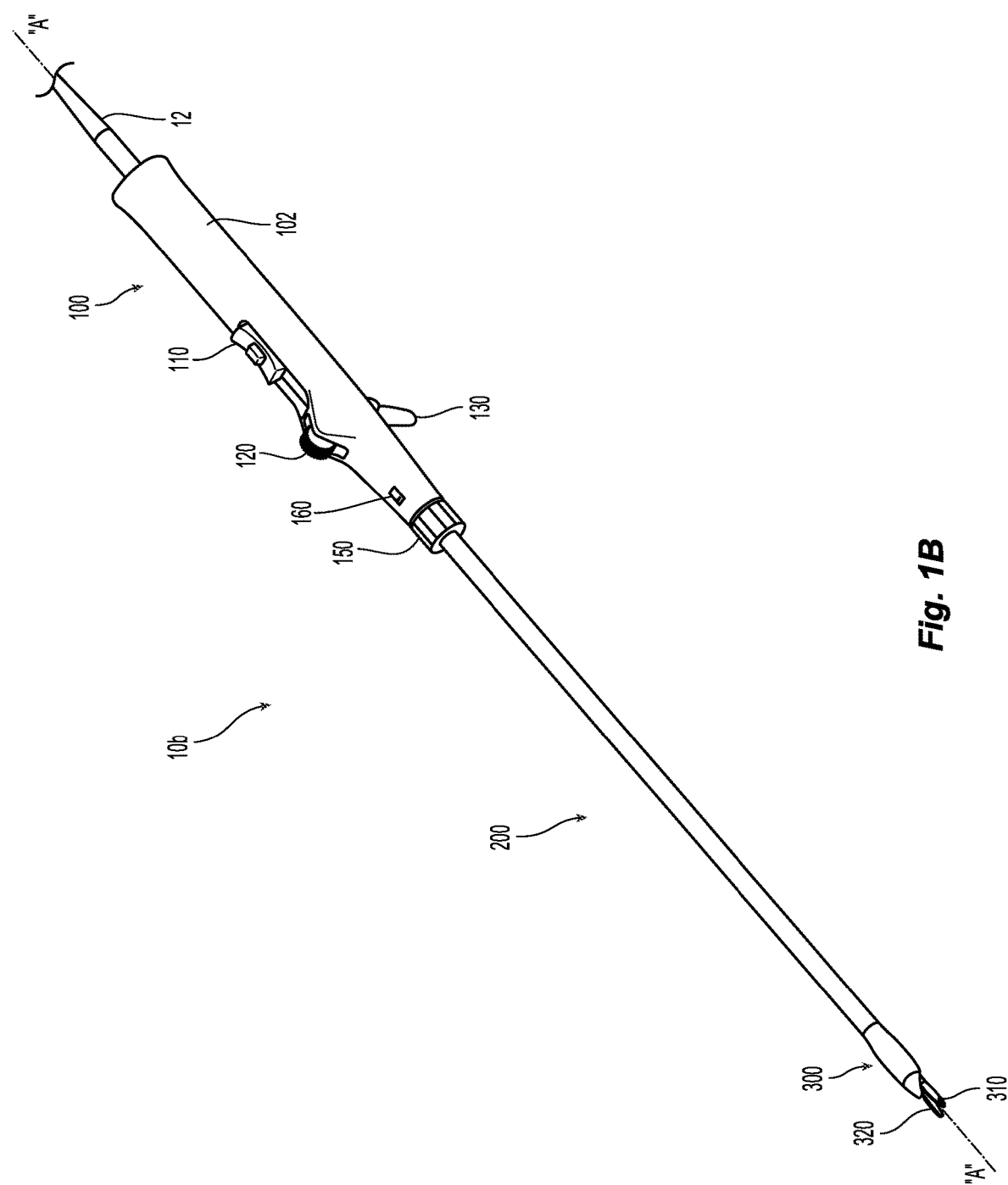
FIG. 1B is a perspective view of an alternative vessel harvesting device in accordance with embodiments of the present disclosure.

Referring initially to FIGS. 1A and 1B, two embodiments of a vein harvesting device are shown for use with various surgical procedures. The vein harvesting device in FIG. 1A is cordless and is referred to as vein harvesting device 10a, and the vein harvesting device in FIG. 1B is corded and is referred to as vein harvesting device 10b. Collectively, vein harvesting devices 10a and 10b are referred to as device 10. Device 10 generally includes a handle assembly 100, an elongated portion 200 defining a longitudinal axis "A-A" that extends distally from handle assembly 100, an end effector 300 disposed at or adjacent a distal end of elongated portion 200, and a visualization device 400 (see FIG. 2).

Device 10 is configured to efficiently remove at least portions of a target vein (e.g., the saphenous vein) while also removing the pedicle layer surrounding the vein to help the viability of the vein after transplantation thereof. Additionally, device 10 is configured to be used endoscopically, e.g., to reduce the chances of infection.

Handle assembly 100 includes a handle housing 102, a first actuation member 110 (e.g., a slide), a second actuation member 120 (e.g., a knob), and a third actuation member 130 (e.g., a trigger).

First actuation member 110 is configured to extend and retract end effector 300 relative to elongated portion 200 and handle housing 102. To extend end effector 300, a user pushes first actuation member 110 in a first direction (e.g., distally), which either distally advances end effector 300 relative to elongated portion 200 and handle housing 102, or retracts elongated portion 200 relative to end effector 300 and handle housing 102.

Second actuation member 120 is configured to open and approximated a pair of jaw members 310, 320 of end effector 300. For example, to open jaw members 310, 320 relative to one another (e.g., move jaw member 310 away from jaw member 320) a user rotates the second actuation member 120 distally, and to close or approximate jaw members 310, 320 (e.g., move jaw member 310 toward jaw member 320), a user rotates second actuation member 120 proximally.

Third actuation member 130 is configured to advance a knife 330 between jaw members 310, 320 to sever tissue therebetween. For instance, moving third actuation member 130 proximally causes knife 330 to advance distally between jaw members 310, 320 to sever tissue, and moving third actuation member 130 distally causes proximal movement or retraction of knife 330.

Additionally, handle assembly 100 may include an activation mechanism or switch 160 (see FIGS. 1A and 1B), where actuation thereof is configured to seal or fuse tissue disposed between jaw members 310, 320 prior to the tissue being severed by knife 330. Alternatively, the sealing or fusing of tissue may also be performed in response to actuation of second actuation member 120. In such an embodiment, actuation of second actuation member 120 would both approximate jaw members 310, 320 onto tissue, and seal the tissue once approximated. An electromechanical switch is envisioned for this purpose and one or more mechanical or electrical features may be employed to ensure the tissue is properly grasped prior to activation. A tone or tactile feedback may be employed to warn the user prior to activation of electrosurgical energy. Mechanical lockouts may also be employed to eliminate the chance of activation when the tributary is not properly secured between the jaw members 310, 320.

Further details of a vessel sealing device including a handle assembly for controlling actuation of an end effector can be found in U.S. Pat. Nos. 7,101,371 and 7,083,618, the entire contents of which being incorporated by reference herein.

Figure 4:
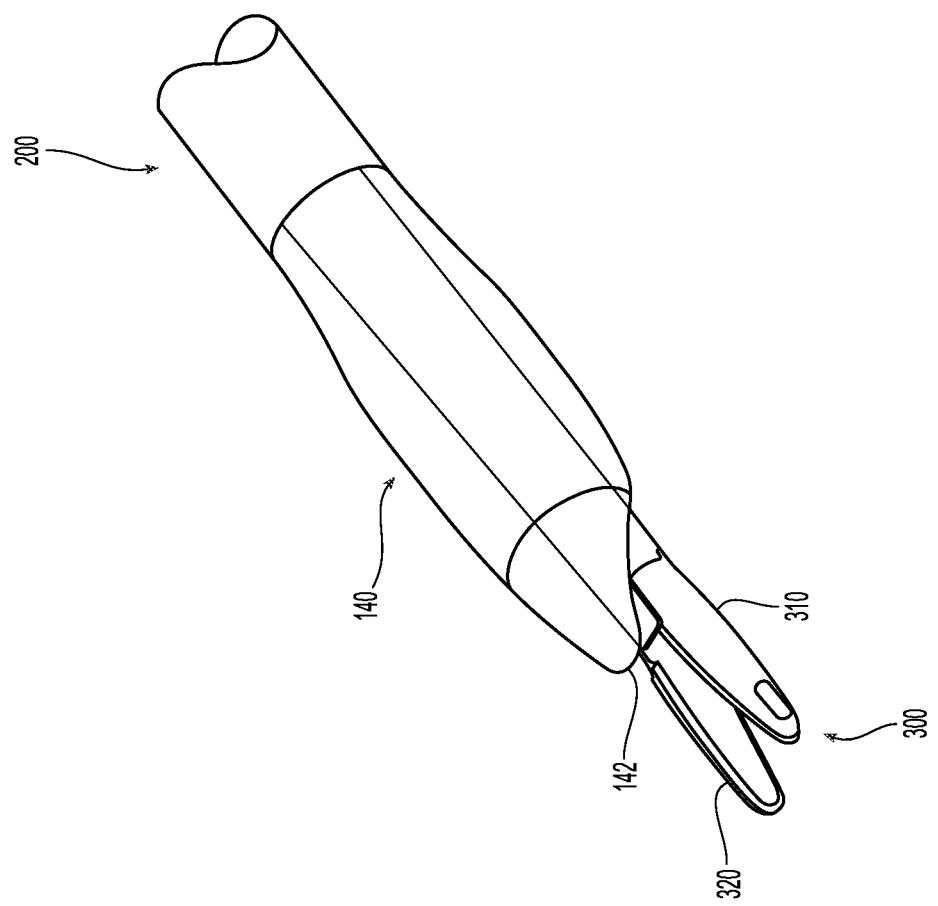
FIG. 4 is an enlarged perspective view of the distal portion of the vessel harvesting device of FIG. 1A, or, alternatively, FIG. 1B, with a pair of jaw members disposed in an extended position.
Figure 3:
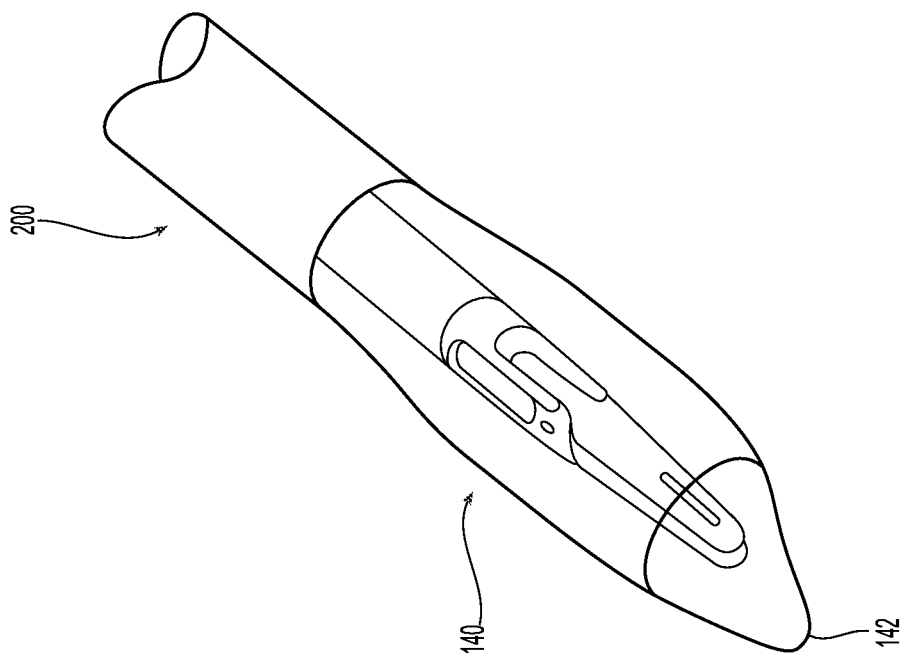
FIG. 3 is an enlarged perspective view of the distal portion of the vessel harvestings device of FIG. 1A, or, alternatively, FIG. 1B, with a pair of jaw members disposed in a retracted position.

With particular reference to FIGS. 2-4, a distal end of elongated portion 200 includes a dissection tip 140. Dissection tip 140 includes a blunt distal end 142 which is configured to dissect (e.g., bluntly dissect), scrape away, or separate tissue as dissection tip 140 is advanced distally. Dissection tip 140 defines an opening 144 configured to allow jaw members 310, 320 of end effector 300 to pass therethrough (when in an approximated position). Dissection tip 140 may be scoop-like in shape, defining a hollow cavity therein. Such a scoop-like shape of dissection tip 140 is configured to scrape tissue away from the target vein while preserving the pedicle. Further, at least a portion of dissection tip 140 is transparent or translucent to allow light to pass therethrough and further enhance visualization in use. More particularly, since dissection tip 140 is optically clear, visualization device 400, which is disposed proximally of at least a portion of dissection tip 140, is able to view and/or capture images and videos of areas located distally of dissection tip 140. Moreover, an optically clear dissection tip 140 allows light to shine therethrough to illuminate the target tissue and/or vein.

Visualization device 400, or camera, is configured to capture and/or record visual data (i.e., images and/or video) from the surgical site and surrounding tissue, and is configured to relay the images and/or video to a display device to help a physician, surgeon, or other visualize the target tissue. The visualization of the target tissue helps ensure that the desired tissue is being clamped, dissected, sealed, severed, etc. by device 10 without the use of an additional instrument (e.g., an endoscope).

Visualization device 400 is configured to communicate with an image sensor, a light source, a processor, and a display device. The display device may be included on device 10 (e.g., handle assembly 100) or may be located remotely (e.g., not on device 10). Additionally, visualization device 400 may be powered by a battery, generator, or battery-powered RF housed at least partially within handle housing 102 (as shown in surgical device 10a of FIG. 1A), or visualization device 400 may be powered by a device located external to handle assembly 100 and connected to handle assembly 100 via a cord 12 (as shown in device 10b of FIG. 1B). Further, device 10b may also include an insufflation tube (not shown) and may be connectable to an insufflation device (not shown) through cord 12.

Further details of a device including a visualization device, a light source, a processor, and heat management techniques are disclosed in commonly-owned International Patent Application No. PCT/CN2017/078143 filed on Mar. 24, 2017, the entire contents of which being incorporated by reference herein.

Device 10 also includes a rotation knob 150 disposed adjacent a distal end of handle assembly 100 and adjacent a proximal end of elongated portion 200. Actuation of rotation knob 150 is configured to cause end effector 300, visualization device 400, and/or elongated portion 200 to rotate about longitudinal axis "A-A" relative to handle assembly 100. Further, since end effector 300 and visualization device 400 are offset from longitudinal axis "A-A" (see FIG. 5), end effector 300 and visualization device 400 move about the longitudinal axis "A-A" (as opposed to simply rotating about the longitudinal axis "A-A").

With reference to FIGS. 6-8E, device 10 includes a constant horizon mechanism 500 disposed in mechanical cooperation with handle assembly 100. Constant horizon mechanism 500 is configured to maintain the level or rotational orientation of visualization device 400 with respect to handle assembly 100 as visualization device 400 is rotated about longitudinal axis "A-A" relative to handle assembly 100. More particularly, constant horizon mechanism 500 is configured to prevent visualization device 400 from rotating about a visualization axis extending longitudinally through a center of visualization device 400.

In particular, constant horizon mechanism 500 includes an elongated tube 510, a first bushing 520, and a second bushing 530. First bushing 520 and second bushing 530 are disposed within handle housing 102. Elongated tube 510 is disposed about visualization device 400, and extends through elongated portion 200. Elongated tube 510 is fixed from rotation relative to visualization device 400. A proximal portion of elongated tube 510 is disposed in mechanical cooperation with first bushing 520. More particularly, elongated tube 510 is engaged to first bushing 520 and is fixed from rotation relative to first bushing 520.

First bushing 520 and second bushing 530 are shaped to limit motion along one axis. In the illustrated embodiments first bushing 520 is a rectangular prism, and second bushing 530 is generally U-shaped having three linear sides. First bushing 520 and second bushing 530 may also include other shapes, such as second bushing including a box-shape having four linear sides. Further, first bushing 520 and second bushing 530 may be shaped (regularly or irregularly) to include at least two parallel sides, such that the combination of shapes would only allow motion perpendicularly to each other.

With particular reference to FIGS. 8A-8E, the relationship between first bushing 520 and second bushing 530 is shown. First bushing 520 is positioned within second bushing 530, and first bushing 520 is constrained to only translate vertically relative to second bushing 530; first bushing 520 is prevented from horizontal translating relative to second bushing 530 due to the relative sizes of first bushing 520 and second bushing 530. Second bushing 530 is disposed within internal walls 103a, 103b, 103c, 103d of handle housing 102. Internal walls 103a, 103b constrain or prevent the vertical movement of second bushing 530 relative to handle housing 102, while internal walls 103c, 103d allow a limited amount of horizontal movement of second bushing 530 relative to handle housing 102. In particular, FIGS. 8A-8E illustrate the relationship of elongated tube 510, first bushing 520, and second bushing 530, relative to handle housing 102, in response to a counter-clockwise rotation of rotation knob 150.

Thus, the engagement between elongated tube 510 and first bushing 520, and the engagement between first bushing 520 and second bushing 530, allow visualization device 400 to be rotated about longitudinal axis "A-A" relative to housing assembly 100, while preventing visualization device 400 from rotating about its own axis. Accordingly, rotation of rotation knob 150 of device 10 causes rotation of jaw members 310, 320 and visualization device 400 about longitudinal axis "A-A" relative to handle assembly 100, while constant horizon mechanism 500 prevents visualization device 400 from rotating about its own axis. Consequently, constant horizon mechanism 500 provides an image with a constant horizon—even during rotation and manipulation of jaw members 310, 320.

The present disclosure also includes methods of performing a surgical procedure, e.g., a vein harvesting procedure, using device 10 discussed herein, and methods of manufacturing device 10 discussed herein. In disclosed methods, while performing a surgical task, end effector 300 and visualization device 400 are rotated about longitudinal axis "A-A" relative to handle assembly 100, while visualization device 400 remains rotationally fixed with regard to the visualization axis extending therethrough.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 9:
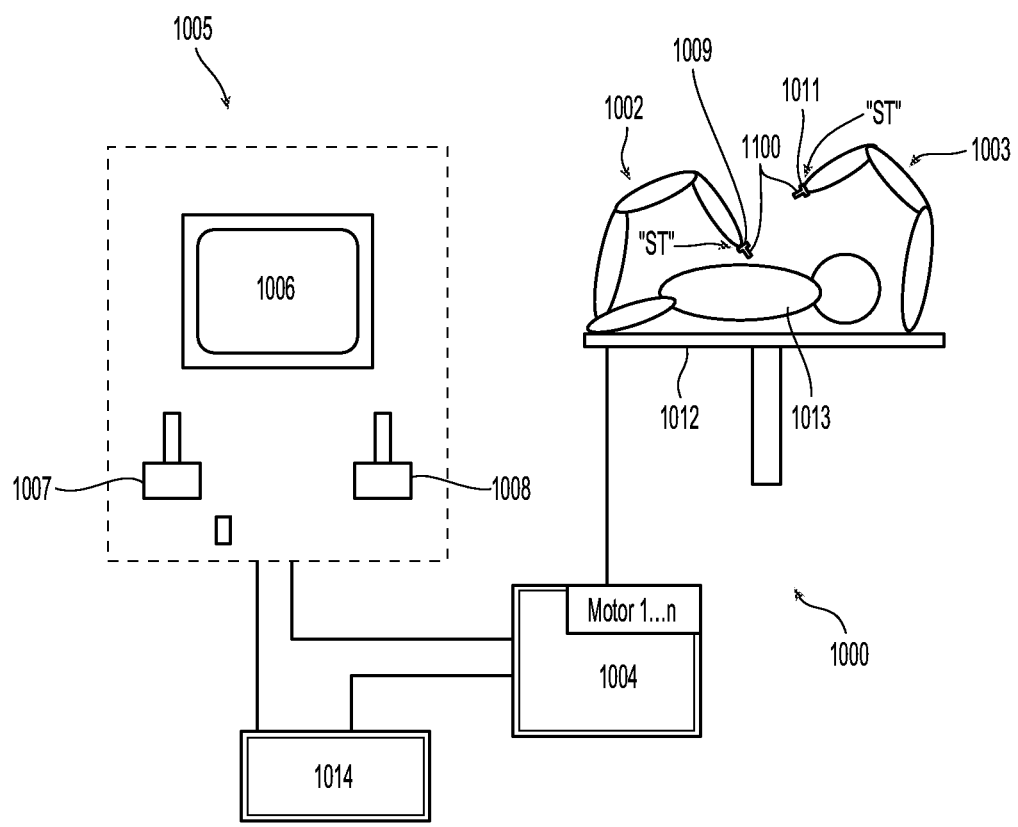
FIG. 9 is a schematic illustration of a surgical system in accordance with the present disclosure.

With particular reference to FIG. 9, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical instrument 10 (including end effector 300) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical device, comprising:
   a handle assembly;
   an elongated portion extending distally from the handle assembly and defining a longitudinal axis;
   an end effector disposed adjacent a distal end of the elongated portion and configured to treat tissue, the end effector rotatable about the longitudinal axis relative to the handle assembly;
   a visualization device defining a visualization axis, a first portion of the visualization device extending through the elongated portion, and a second portion of the visualization device disposed at least partially within the handle assembly, the visualization device rotatable about the longitudinal axis relative to the handle assembly; and
   a constant horizon mechanism disposed in operative engagement with the visualization device and configured to prevent the visualization device from rotating about the visualization axis when the visualization device rotates about the longitudinal axis, the constant horizon mechanism including an elongated tube, a first bushing, and a second bushing, the elongated tube extending through the elongated portion and disposed about the visualization device, the elongated tube fixed from rotation about the longitudinal axis relative to the visualization device.

2. The surgical device according to claim 1, wherein the first bushing and the second bushing are disposed within the handle assembly.

3. The surgical device according to claim 2, wherein a proximal portion of the elongated tube is operatively connected to the first bushing.

4. The surgical device according to claim 2, wherein the elongated tube is fixed from rotation about the longitudinal axis relative to the first bushing.

5. The surgical device according to claim 2, wherein the first bushing includes at least two parallel sides.

6. The surgical device according to claim 5, wherein the second bushing includes at least two parallel sides.

7. The surgical device according to claim 1, wherein the first bushing is disposed at least partially within the second bushing, and wherein the first bushing is fixed from lateral movement relative to the second bushing.

8. The surgical device according to claim 7, wherein the second bushing is fixed from vertical movement relative to the handle assembly.

9. The surgical device according to claim 8, wherein a proximal portion of the elongated tube is operatively connected to the first bushing, and wherein the elongated tube is fixed from rotation about the longitudinal axis relative to the first bushing.

10. The surgical device according to claim 1, wherein the visualization axis is offset from the longitudinal axis.

11. The surgical device according to claim 10, wherein the visualization axis is parallel to the longitudinal axis.

12. The surgical device according to claim 1, wherein the first bushing is a rectangular prism, and wherein the second bushing is generally U-shaped having three linear sides.

* * * * *